US00PP23608P2

(12) United States Plant Patent
Bradford

(10) Patent No.: US PP23,608 P2
(45) Date of Patent: May 21, 2013

(54) NECTARINE TREE NAMED 'PEARLICIOUS VII'

(50) Latin Name: *Prunus persica*
Varietal Denomination: Pearlicious VII

(76) Inventor: Lowell Glen Bradford, Le Grand, CA (US)

( * ) Notice: Subject to any disclaimer, the term of this patent is extended or adjusted under 35 U.S.C. 154(b) by 11 days.

(21) Appl. No.: 13/374,009

(22) Filed: Dec. 8, 2011

(51) Int. Cl.
*A01H 5/00* (2006.01)

(52) U.S. Cl.
USPC ..... Plt./188

(58) Field of Classification Search ..... Plt./188
See application file for complete search history.

(56) References Cited

U.S. PATENT DOCUMENTS

PP9,360 P 11/1995 Bradford
PP14,249 P2 10/2003 Bradford

*Primary Examiner* — Kent L Bell

(57) ABSTRACT

The present invention relates to a new and distinct variety of nectarine tree, *Prunus persica*, broadly characterized by a large size, very vigorous, hardy, self-fertile, productive and regular bearing tree. The variety blooms between the early to mid season and requires about 550 chilling hours. The fruit matures under the ecological conditions described in early July, with first picking on Jul. 7, 2011. The fruit is uniformly large in size, globose in shape, clingstone in type, firm and melting in texture, white in flesh color, full red in skin color, and a tasty balance of acid and sugar in flavor.

1 Drawing Sheet

Botanical classification: *Prunus persica.*
Variety denomination: 'Pearlicious VII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'Pearlicious VII'.

The present variety was hybridized by me in 2001 as a first generation cross using 'June Pearl' (U.S. Plant Pat. No. 9,360) nectarine as the selected seed parent and an unnamed yellow flesh nectarine designated by code number '1P1152' (unpatented) as the selected pollen parent. The fruit of this cross was gathered in the spring of 2001, and the seeds were removed from the fruit, germinated, stratified, and grown as seedlings on their own root in my greenhouse. Upon reaching dormancy that winter, the seedlings were transplanted as a group to a cultivated area of my experimental orchard located near Le Grand, Calif., in Merced County (San Joaquin Valley). During the fruit evaluation season of 2005 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'June Pearl' nectarine (U.S. Plant Pat. No. 9,360) by producing nectarines that are mostly red in skin color, white in flesh color, clingstone in type, firm in texture, but is distinguished therefrom by producing fruit that is larger in size, sweeter in flavor, more symmetrical and globose in shape, and that matures about fourteen days later.

The present variety is similar to its pollen parent, '1P1152' nectarine by producing fruit that is clingstone in type, nearly full red in skin color, and large in size, but is quite distinguished therefrom by being white in flesh color instead of yellow, by being larger in size, and by maturing about thirty days later.

The present variety is most similar to 'Candy Pearl' (U.S. Plant Pat. No. 14,249) nectarine by producing nectarines that are white in flesh color, clingstone in type, firm in texture, large in size, full red in skin color, and mature in early July, but is distinguished therefrom by blooming earlier, by requiring less chilling hours, by having globose instead of reniform leaf glands, and by producing fruit that has a bitter instead of sweet kernel, that is more symmetrical, and that is sweeter and lightly acidic instead of sub-acidic in flavor.

SUMMARY OF VARIETY

In summary, the present nectarine variety is characterized by a large size, very vigorous, hardy, self-fertile, productive and regular bearing tree. The variety blooms between the early to mid season and requires about 550 chilling hours. The fruit matures under the ecological conditions described in early July, with first picking on Jul. 7, 2011. The fruit is uniformly large in size, globose in shape, clingstone in type, firm and melting in texture, white in flesh color, full red in skin color, and a tasty balance of acid and sugar in flavor.

DRAWING

The accompanying photograph consists of four whole fruits positioned to display the characteristics of the skin color and form, one divided fruit to reveal the flesh and stone, a typical young tip shoot, characteristic leaves, and three insets to reveal buds and a blossom.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 12, 2011, on the original tree during its tenth growing season. The blossom and flower descriptions were made the previous blooming season. All major color code designations are by reference to the Inter-Society Color Council, National Bureau of Standards. Common color names are also used occasionally.

PARENTAGE

Seed parent: 'June Pearl' nectarine (U.S. Plant Pat. No. 9,360).

Pollen parent: '1P1152' nectarine (unpatented).

TREE

Size: Large, reaching and maintaining a height of 9' [2.74 m.] and a spread of 11' [3.35 m.] after ten growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Approximate chilling requirement: 550 hours.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

- *Size*.—Medium, reaching a maximum diameter of 6½" [165.1 mm.] after the tenth growing season.
- *Texture*.—Shaggy.
- *Bark color*.—A Grayish brown [61. gy.Br] and Moderate brown [58. m.Br] variegation with a few Moderate orange yellow [71. m.OY] crevices.
- *Lenticels*.—Approximate Number Per Square Inch: 12. Color: Light yellowish brown [76. l.yBr]. Average Size: ¼" [6.4 mm.]. Shape: Eye-shaped, elongated.

Branches:

- *Size*.—Diameter of main scaffold is 4½" [114.3 mm.] measured 12" above the crotch, diameter of limb is 2¼" [57.2 mm.] measured 12" above the first fork.
- *Texture*.—Smooth on first year wood, increasing roughness with age.
- *Color*.—Second Year Wood: Moderate yellowish brown [77. m.yBr]. Third Year Wood: Deep yellowish brown [75. deep yBr].
- *Lenticels*.—Number Per Square Inch: About 80 on second year wood. Color: Light yellowish brown [76. l.yBr]. Average size: 1/64" [0.4 mm.] to 1/16" [1.6 mm.] on second year wood. Shape: Eye-shaped, elongated.

Leaves:

- *Size*.—Large. Average Length: 6½" [165.1 mm.]. Average Width: 1½" [38.1 mm.].
- *Arrangement*.—Alternate.
- *Thickness*.—Medium.
- *Form*.—Elliptical.
- *Apex*.—Acuminate.
- *Base*.—Rounded to obtuse.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Vein color*.—Pale yellow green [121. p.YG].
- *Petiole*.—Average Length: ⅜" [9.5 mm.]. Average Thickness: 1/16" [1.6 mm.]. Color: Strong yellow green [117. s.YG].
- *Stipules*.—Number: Usually 2 per leaf, up to 6 per growing tip. Average Length: ¼" [6.4 mm.]. Color: Moderate yellow green [120. m.YG] becoming Moderate olive green [125. m.OlG] with maturity.
- *Glands*.—Number: 1 to 4 per leaf. Position: Mostly opposite. Size: Medium. Form: Globose. Color: Strong yellow green [117. s.YG] becoming Moderate reddish brown [43. m.rBr] with age.
- *Leaf buds*.—Pointed, medium in size.

Flower buds:

- *Hardiness*.—Hardy, with respect to central California winters.
- *Diameter*.—Typically ⅜" [9.5 mm.] 1 week before bloom.
- *Length*.—Typically ¾" [15.9 mm.] 1 week before bloom.
- *Form*.—Not appressed.
- *Surface*.—Pubescent.
- *Tip color*.—Strong purplish pink [247. s.pPk].

Flowers: Perfect, complete, perigynous, usually a single pistil, about thirty stamens, five sepal and petal locations alternately positioned.

- *Type*.—Showy, large.
- *Average flower diameter*.—2" [50.8 mm.].
- *Number of petals*.—Mostly five, extra petal fragments are common.
- *Petal shape*.—Circular to oval.
- *Petal margin*.—Entire, wavy.
- *Average petal diameter*.—¾" [19.1 mm.].
- *Average petal length*.—13/16" [20.6 mm.].
- *Petal apex*.—Rounded.
- *Petal base*.—Rounded to somewhat truncate.
- *Petal color*.—Light pink [4. l.Pk] on both sides.
- *Anther color*.—Deep reddish orange [36. deep rO] over a Light yellow [86. l.Y] center at bloom onset.
- *Stigma color*.—Light greenish yellow [101. l.gY].
- *Sepal color*.—Dark purplish red [259. d.pR] on the outer surface.
- *Sepal length*.—¼" [6.4 mm.].
- *Sepal width*.—3/16" [4.8 mm.].
- *Sepal apex*.—Rounded to elliptical to match the sepal length and width.
- *Sepal margin*.—Fairly smooth.

*Average pistil length.*—¾" [19.1 mm.].
*Average stamen length.*—9/16" [14.3 mm.].
*Fragrance.*—Moderate.
*Blooming period.*—Early to mid season, two days after 'Spring Bright' (U.S. Plant Pat. No. 7,507) nectarine.
*Onset of bloom.*—One percent on Feb. 22, 2011.
*Date of full bloom.*—Mar. 5, 2011.
*Duration of bloom.*—One to two weeks, dependent on ambient temperature.
*Number per cluster.*—1 to 3 with single flowers most common.

FRUIT

Maturity when described: Firm ripe, Jul. 12, 2011.
Date of first picking: Jul. 7, 2011.
Date of last picking: Jul. 21, 2011.
Size: Uniform, large.
*Average diameter axially.*—2¾" [69.9 mm.].
*Average diameter across cheek plane.*—2 15/16" [74.6 mm.].
*Average diameter across suture plane.*—3" [76.2 mm.].
*Typical weight.*—8.2 ounces [232.5 grams].
Form: Uniform, globose, compressed axially, fairly symmetrical.
*Longitudinal section form.*—Round.
*Transverse section through diameter.*—Round.
Suture: Extends from the base, continues along the side, and ends just past the pistil point.
*Near the base.*—A sharp groove.
*Along the side.*—A shallow trough.
*Near the apex.*—A shallow groove.
Ventral surface: Rounded, lipped throughout on both sides.
Lips: Slightly unequal.
Cavity: Flaring, slightly elongated in the suture plane, suture showing on one side, Pale yellow green [121. p.YG] stem markings typical.
*Depth.*—⅝" [15.9 mm.].
*Breadth.*—1⅛" [28.6 mm.].
Base: Truncate, strongly cordate if viewed parallel to the suture.
Apex: Truncate, cordate if viewed parallel to the suture.
Pistil point: Slightly apical, short in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—None observed in a dry season.
*Color.*—Dark red [16. d.R] over a Strong red [12. s.R] background with Pale orange yellow [73. p.OY] freckling throughout.
Flesh:
*Color.*—Yellowish white [92. yWhite], with a minor amount of Light pink [r. l.Pk] streaking very close to the stone.
*Surface of pit cavity.*—Covered with Light yellowish pink [28. l.yPk] broken fibers when twisted from the stone.
*Amygdalin.*—Moderate.
*Juice.*—Moderate, rich.
*Texture.*—Firm, tough, crisp.
*Fibers.*—Few, fine, tender.
*Ripens.*—Slightly uneven, earliest at the apex.
*Flavor.*—A nice balance of sugar and acid, typically 18 to 20 brix.
*Aroma.*—Moderate.
*Eating quality.*—Very good.

STONE

Type: Clingstone.
Form: Oval.
Hilum: Narrow, oval.
Base: Obtuse, slightly rounded.
Apex: Acuminate.
Sides: Equal.
Surface: Irregularly furrowed toward the apex, pitted toward the base.
Ridges: Rounded.
External color: Moderate reddish brown [43. m.rBr].
Pit wall color when cracked: Pale yellow green [121. p.YG].
Cavity surface color: Light yellow green [119. l.YG].
Average pit wall thickness: ¼" [6.4 mm.].
Average width: 1 1/16" [27 mm.].
Average length: 1⅝" [41.3 mm.].
Average breadth: ¾" [19.1 mm.].
Tendency to split: None observed.
Kernel:
*Form.*—Oval.
*Skin color.*—Pale yellow [89. p.Y] when first removed.
*Pellicle color.*—Light yellow [86. l.Y].
*Vein color.*—Light yellow [86. l.Y].
*Taste.*—Bitter.
*Viable.*—Yes.
*Average width.*—½" [12.7 mm.].
*Average length.*—¾" [19.1 mm.].
*Amygdalin.*—Moderate.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Candy Pearl' (U.S. Plant Pat. No. 14,242) nectarine by producing nectarines that are white in flesh color, clingstone in type, firm in texture, large in size, full red in skin color, and mature in early July, but is distinguished therefrom by blooming earlier, by requiring less chilling hours, by having globose instead of reniform leaf glands, and by producing fruit that has a bitter instead of sweet kernel, that is more symmetrical, and that is sweeter and lightly acidic instead of sub-acidic in flavor.

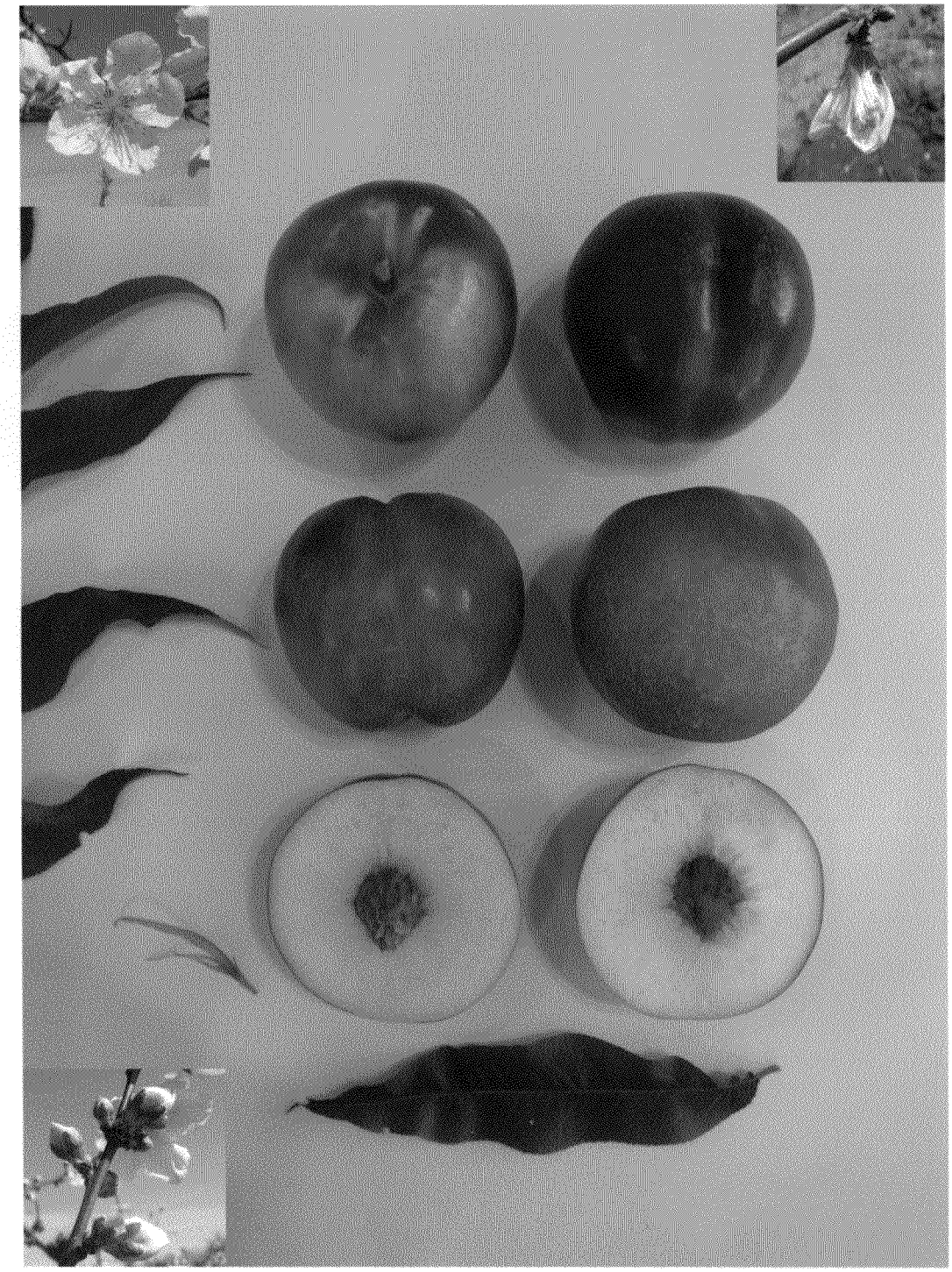

* * * * *